(12) United States Patent
McKay et al.

(10) Patent No.: US 8,506,646 B2
(45) Date of Patent: Aug. 13, 2013

(54) MULTI-PURPOSE MEDICAL IMPLANT DEVICES

(75) Inventors: William F. McKay, Memphis, TN (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 984 days.

(21) Appl. No.: 11/118,081

(22) Filed: Apr. 29, 2005

(65) Prior Publication Data

US 2006/0247791 A1 Nov. 2, 2006

(51) Int. Cl.
*A61F 2/28* (2006.01)

(52) U.S. Cl.
USPC .................................. 623/23.51; 623/23.61

(58) Field of Classification Search
USPC .......... 623/11.11, 13.18, 16.11, 17.11, 20.15, 623/20.16, 20.17, 23.47, 23.51, 23.5, 23.55, 623/23.58, 23.61, 23.71, 23.75, 23.63
See application file for complete search history.

(56) References Cited

U.S. PATENT DOCUMENTS

| | | |
|---|---|---|
| 4,013,078 A | 3/1977 | Feild |
| 4,394,370 A | 7/1983 | Jefferies |
| 4,516,276 A | 5/1985 | Mittelmeier et al. |
| 4,743,229 A | 5/1988 | Chu |
| 4,776,890 A | 10/1988 | Chu |
| 4,780,450 A | 10/1988 | Sauk et al. |
| 4,865,602 A | 9/1989 | Smestad et al. |
| 4,888,366 A | 12/1989 | Chu et al. |
| 4,992,226 A | 2/1991 | Piez et al. |
| 5,001,169 A | 3/1991 | Nathan et al. |
| 5,035,715 A | 7/1991 | Smestad et al. |
| 5,123,925 A | 6/1992 | Smestad et al. |
| 5,231,169 A | 7/1993 | Constantz et al. |
| 5,246,457 A | 9/1993 | Piez et al. |
| 5,273,964 A | 12/1993 | Lemons |
| 5,425,770 A | 6/1995 | Piez et al. |
| 5,439,464 A | 8/1995 | Shapiro |
| 5,562,736 A | 10/1996 | Ray et al. |
| 5,573,771 A | 11/1996 | Geistlich et al. |

(Continued)

FOREIGN PATENT DOCUMENTS

| | | |
|---|---|---|
| DE | 19943594 | 4/2001 |
| EP | 0309241 | 3/1989 |

(Continued)

OTHER PUBLICATIONS

Keating, J.F., McQueen, M.M., "Substitutes for Autologous Bone Graft in Orthopaedic Trauma", *J Bone Joint Surg.*, vol. 83-B, No. 1, Jan. 2001, pp. 3-8.

*Primary Examiner* — David Isabella
*Assistant Examiner* — Randy Shay
(74) *Attorney, Agent, or Firm* — Sorell Lenna & Schmidt LLP

(57) ABSTRACT

Described are medical devices for supporting or inducing bone growth including an implant body defining one or more separation-assist lines that facilitate separation of the body into two or more substantially pre-defined pieces. The implant body can be used and implanted as a whole or may be separated into multiple pieces, some or all of which can be used at one or multiple implant sites in a patient. Separation-assist lines in implant bodies can serve a dual role in imparting increased and controlled flexibility to the overall body when used as a whole at an implant site. Also described are methods of making and using, and kits including, such medical devices.

18 Claims, 3 Drawing Sheets

(56) References Cited

U.S. PATENT DOCUMENTS

| | | | |
|---|---|---|---|
| 5,702,449 | A | 12/1997 | McKay |
| 5,776,193 | A | 7/1998 | Kwan et al. |
| 5,785,710 | A | 7/1998 | Michelson |
| 5,868,745 | A | 2/1999 | Aleyne |
| 5,972,368 | A * | 10/1999 | McKay .................. 424/423 |
| 6,066,325 | A * | 5/2000 | Wallace et al. .......... 424/400 |
| 6,395,007 | B1 | 5/2002 | Bhatnagar et al. |
| 6,413,278 | B1 | 7/2002 | Marchosky |
| 6,454,767 | B2 | 9/2002 | Alleyne |
| 6,454,811 | B1 * | 9/2002 | Sherwood et al. ....... 623/23.76 |
| 6,541,037 | B1 | 4/2003 | Lee et al. |
| 6,652,593 | B2 * | 11/2003 | Boyer et al. ........... 623/23.63 |
| 6,858,015 | B2 | 2/2005 | List |
| 2001/0034527 | A1 | 10/2001 | Scribner et al. |
| 2001/0036498 | A1 * | 11/2001 | Blaschke et al. ......... 426/496 |
| 2001/0037091 | A1 | 11/2001 | Wironen et al. |
| 2002/0026244 | A1 | 2/2002 | Trieu |
| 2002/0049448 | A1 | 4/2002 | Sand et al. |
| 2002/0082605 | A1 | 6/2002 | Reiley et al. |
| 2002/0082694 | A1 * | 6/2002 | McKay .................. 623/17.11 |
| 2002/0138145 | A1 | 9/2002 | Marchosky |
| 2003/0004491 | A1 | 1/2003 | Tenhuisen et al. |
| 2003/0236573 | A1 | 12/2003 | Evans et al. |
| 2004/0030345 | A1 | 2/2004 | Aurin et al. |
| 2004/0034434 | A1 | 2/2004 | Evans et al. |
| 2004/0064193 | A1 | 4/2004 | Evans et al. |
| 2004/0122429 | A1 | 6/2004 | Phillips et al. |
| 2004/0127987 | A1 | 7/2004 | Evans et al. |
| 2004/0138758 | A1 | 7/2004 | Evans et al. |
| 2004/0254538 | A1 | 12/2004 | Murphy et al. |
| 2005/0043819 | A1 * | 2/2005 | Schmidt et al. ......... 623/23.72 |
| 2005/0214340 | A1 * | 9/2005 | Erbe et al. ............. 424/423 |

FOREIGN PATENT DOCUMENTS

| | | |
|---|---|---|
| EP | 0428378 | 5/1991 |
| EP | 0530804 | 3/1993 |
| EP | 0747067 | 12/1996 |
| EP | 1477202 | 11/2004 |
| GB | 1584080 | 2/1981 |
| WO | WO 89/04646 | 6/1989 |
| WO | WO 96/39203 | 12/1996 |
| WO | WO 97/31661 | 9/1997 |
| WO | WO 97/40137 | 10/1997 |
| WO | WO 98/17330 | 4/1998 |
| WO | WO 03/009884 | 2/2003 |
| WO | WO 03/026522 | 4/2003 |
| WO | WO 2004/014263 | 2/2004 |
| WO | WO 2004/054633 | 7/2004 |

* cited by examiner ial implant device that can be put to any of multiple modes of use by a physician or other caregiver in the operational field. Thus, in one embodiment, the present

MULTI-PURPOSE MEDICAL IMPLANT DEVICES

BACKGROUND OF THE INVENTION

The present invention relates generally to a medical device including an implant material for introduction into a patient. In particular aspects, the present invention relates to medical devices for supporting or promoting bone growth that include an implant body formed of an osteoconductive or osteoinductive material.

As further background, a variety of implants materials have been suggested for use in patients, including materials for the support or induction of bone growth. As examples, some implant materials have included minerals such as ceramic bodies which are sized for implant into a location of the patient. Other implant matrices have been spongy devices made from organic substances such as collagen or other natural or synthetic polymers. In still further developments, implant materials have been developed which include both an organic carrier material such as a fibrous- or gel-form organic carrier, combined with a particulate mineral component incorporated within the organic carrier.

While implant materials such as those discussed above have been taught, there is relatively less effort reflected in literature to creating medical devices that include implant materials and which may be used in a variety of ways and for multiple purposes. As well, there are needs in the art for medical devices incorporating implant materials that provide benefits in manufacture, packaging, handling and similar operations. The present invention is addressed to these needs.

SUMMARY OF THE INVENTION

In one aspect, the present invention provides an advantageous medical implant device that can be put to any of multiple modes of use by a physician or other caregiver in the operational field. Thus, in one embodiment, the present invention provides a multi-purpose medical implant device that comprises a biocompatible, three-dimensional osteoconductive or osteoinductive implant body including mineral-containing particles incorporated within an organic carrier, the body including an upper surface, a lower surface, and side walls interconnecting the upper surface and the lower surface. At least one separation-assist line is defined in the implant body, the separation-assist line configured to facilitate separation of a first implant body portion from a second implant body portion. In this manner, a single implant body can be manufactured, packaged and provided to a caregiver in a kit or otherwise, and the implant body may be used either in its entirety at an implant site, or may be manipulated by the caregiver to separate the implant body into multiple smaller pieces, some or all of which may be used, at a single implant site or at multiple different implant sites. The present invention also affords the caregiver an ability to conveniently adjust the size of the implant based upon the size of the defect to be filled or other factors noted in the operational field, which can help to assure that an implant volume of an appropriate size is used. For example, this can help to assure that the use of an inappropriately oversized implant body is avoided, e.g. one which would be packed into a defect under too much compression thus potentially leading to an undesired increase in the spatial density or concentration of an osteoconductive and/or osteoinductive material in the implant body, and/or creating too much compression on surrounding soft or hard tissues, or that the use of an inappropriately undersized implant body is avoided, e.g. one that would be packed into a defect too loosely.

In another aspect, the present invention provides a method for treating a patient in need of bone growth, the method comprising providing a medical implant device that includes a biocompatible, three-dimensional osteoconductive or osteoinductive implant body including mineral-containing particles incorporated within an organic carrier, the body including an upper surface, a lower surface, and side walls interconnecting the upper surface and the lower surface, the body further defining at least one separation-assist line; and, implanting all or at least one portion of said implant body into the patient at a site where bone growth is desired.

The present invention also provides a medical kit for treating a patient, the kit including at least a medical implant device as described above and a package enclosing the medical implant device in a sterile condition.

In a further aspect, the present invention provides a method for manufacturing a medical implant device, comprising forming a biocompatible, three-dimensional osteoconductive or osteoinductive implant body including mineral-containing particles incorporated within an organic carrier, the body including an upper surface, a lower surface, and side walls interconnecting the upper surface and the lower surface; and, providing in the implant body at least one separation-assist line configured to facilitate separation of the first implant body portion from the second implant body portion. The one or more separation assist lines can be provided in the implant body after it is formed and/or as it is formed. For example, molded or cast implant bodies can be formed, wherein the mold or cast includes adaptations such as walls, posts, or other structures that define the separation-assist line in the implant body as it is being formed.

Additional embodiments as well as features and advantages of the present invention will be apparent from the descriptions herein.

DETAILED DESCRIPTION

Figure 1:
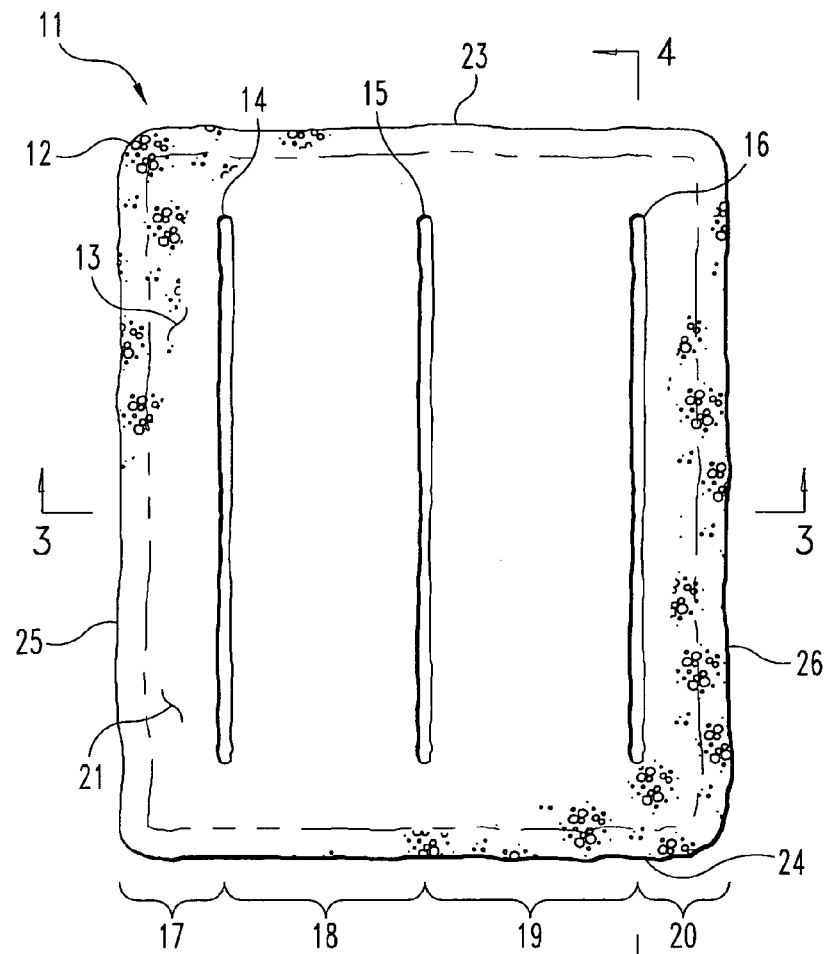
FIG. 1 provides a top view of an illustrative medical implant body of the present invention defining a plurality of score lines.
Figure 2:
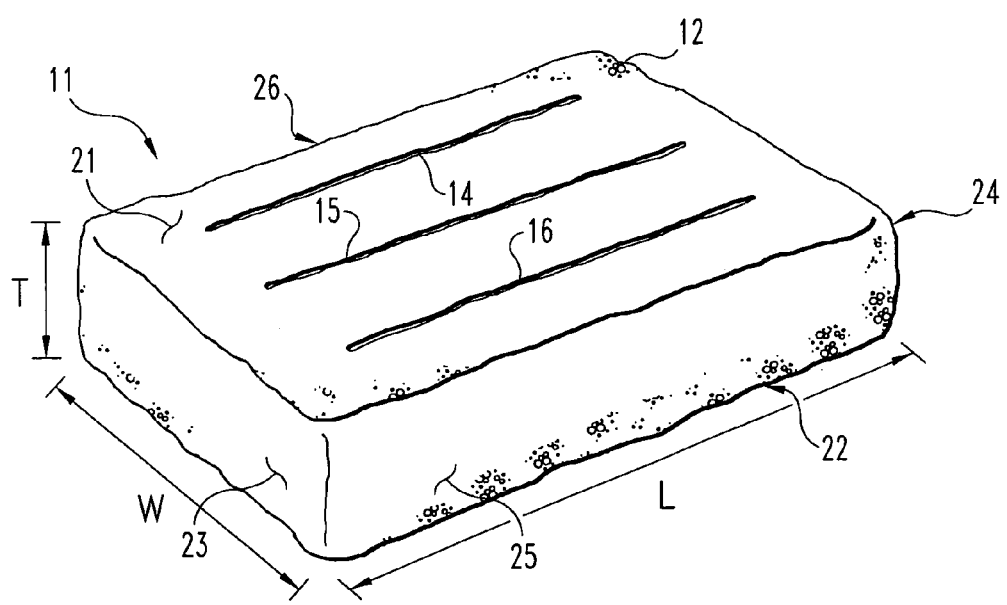
FIG. 2 provides a perspective view of the medical implant body of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, the present invention provides unique medical devices that include implant bodies with one or more separation-assist lines defined therein. The present invention also includes methods of making and of using the unique medical devices of the invention, and kits incorporating the same.

In advantageous embodiments of the invention, the implant material used in the medical device will be an osteoconductive or osteoinductive material. The implant material used to form the implant body can be partially or completely resorbable. As to other properties, beneficial implant materials will be flexible or otherwise deformable, with the ability to conform at least to some extent to a defect or other implant site at which bone growth is desired in a patient to be treated. Still further, the implant material can in certain embodiments serve as a scaffolding material for tissue ingrowth. In certain inventive aspects, the implant material is flexible yet resistant to compression under the forces that would usually be imparted by soft tissues surrounding an implant site where bone growth is desired.

As noted above, medical devices of the invention will include implant bodies which include a separation-assist functionality, whereby the implant body can be separated along a predetermined region into multiple pieces or constituent implant bodies of the overall implant body. In this regard, the implant body may include a separation-assist line such as that provided by a score or perforation line, wherein the ability to break or tear the implant body along that line is enhanced relative to the ability to break or tear the implant body along regions on either side of the separation-assist line. Combinations of separation-assist structures can be used, for example wherein both score lines and perforation lines or other means are used together to provide an overall implant body that can be beneficially separated into multiple pieces.

The score, perforation and/or other separation-assist line or lines can extend partially or completely across a dimension of the implant body, or combinations of separation assist lines that extend partially and completely across a dimension of the implant body can be used. In especially desirable embodiments of the invention, the separation-assist line or lines extend only partially across the implant body, thereby leaving a band or swath of implant material that lacks the separation-assist line (e.g. at one or more peripheral outer regions) which can impart a greater overall structural integrity to the implant body. This may, for example, assist in assuring that accidental separation does not occur in manufacture, packing, or handling operations. This may also be used to control the extent to which the separation-assist line or lines impact the overall flexibility of an implant body.

As to further features of the separation-assist line, in some embodiments, the separation-assist line will be provided by a score line that extends from a surface of the implant body and penetrates at least partially through the thickness of the implant body. For example, a score line may extend at least about ten percent through a thickness of the implant body, and typically in the range of about 10% to about 80% through the thickness of the implant body. In certain forms, such a score line will extend about 20% to about 60% through the thickness of the implant body. As well, implant bodies can be provided with corresponding score lines penetrating the thickness of the implant body from opposed locations, thus leaving an amount of implanted material centrally located within the implant body connecting the separable pieces of the implant body (see e.g. FIG. 7 and discussion below).

Separation-assist lines can also be provided by perforations that include a plurality of spaced holes or slits in the implant material, wherein intact implant material is located in regions between the slits or holes extending partially or completely through the implant body. In other embodiments, a separation assist line or lines can include a material having the same thickness as surrounding regions but being more fragile, tearable or breakable than the surrounding regions, e.g. being less dense or made of a material with physical properties that are distinguished from those of the surrounding regions. Each of these separation-assist measures and others, as well as combinations thereof, can be used in medical devices of the present invention.

Implant bodies of the present invention are configured to be separated into two or more pieces, for example, into two to ten pieces. It will be understood, however, that implant bodies separable into more pieces are contemplated as falling within the present invention. As well, the pieces into which the implant body is separable may be the same as each other, or may be different from each other, or combinations of these can be provided in an overall implant body with separation-assist functionality. For example, the volumes of the separable pieces may be generally the same or may differ from one another, and the shapes of the separable pieces may be the same or may be different from each other. The separable pieces may for example be polygonal in shape including rectangles (squares and otherwise), triangles, trapezoids, etc., rounded or circular in shape, convoluted in shape, etc. Correspondingly, the separation-assist line or lines in the implant bodies of the invention can be straight, curved, cornered, convoluted, or combinations of any of these or other configurations to achieve the desired properties in the implant body.

The width of the material interruption or differential properties of separation-assist lines in devices of the invention can vary widely but will typically be in the range of up to about 1 cm, for example about 0.1 mm to 1 cm. The width of the separation-assist line will more typically be in the range of about 0.5 mm to about 5 mm. The separation-assist score or other structure can be defined perpendicularly to an outer surface of the implant body or at another angle relative thereto. Illustratively, the separation-assist score or perforation or other structure may extend so as to define an angle between 45 and 90 degrees relative to a surface at which the structure begins, and more typically will define an angle between about 70 and 90 degrees relative to a surface from which it extends. It will be understood in this regard that such angles are discussed in a general sense and that as it extends through a thickness of the implant body, the separation-assist structure can itself take a convoluted or rounded path and thus is not necessarily straight or planer in character. In general, any separation-assist lines that effectively lead to a separation of the implant body in a predetermined region are contemplated as falling within the invention. As well, the separation can be achieved by any suitable mechanism including a sharp break or fracture, a tear, or a phenomenon in between or combining these or other mechanisms.

With reference now to the Figures, shown in FIGS. 1-4 is a first illustrative embodiment of a medical device of the present invention. In particular, shown is medical device 11 including implant body 12 comprised of a biocompatible implant material 13. Implant body 12 includes 3 score lines 14, 15, and 16, rendering the medical device 11 separable in to implant body pieces 17, 18, 19, and 20. Implant body 12 includes an upper surface 21, a lower surface 22, and side walls 23, 24, 25, and 26. In the illustrated device 11, a rectangular configuration is provided. This may include for example an equilateral rectangle (square) configuration wherein walls 23-26 each have the same dimension, or a non-equilateral rectangle wherein walls 23 and 24 are of a lesser dimension than walls 25 and 26. Thus, overall implant body 12 includes a length L, defined as the dimension of walls 25 and 26 in a first direction, a width W defined by the dimension of walls 23 and 24 in a first direction, and a thickness T defined by the dimension of walls 23-26 in a second direction generally perpendicular to the first directions noted above.

In certain embodiments of the invention, the length L of the implant body will range from about 2 cm to about 20 cm, the width W will range from about 2 cm to about 20 cm, and the thickness T will range from about 1 cm to about 10 cm. More typically, length L will range from about 5 to 15 cm, width W will range from about 5 to 15 cm, and thickness T will range from about 2 to about 15 cm.

As to volume, advantageous implant bodies 12 of the invention can have a total volume of at least about 2 cubic centimeters (cc), e.g. in the range of about 2 cc to about 100 cc, and more typically in the range of about 10 cc to about 50 cc, although both smaller and larger overall volumes may also be used in the present invention. Similarly, the volume of the pieces into which the implant bodies are configured to be separated may range from about 1 cc to about 50 cc, more typically in the range of about 5 cc to about 20 cc, although other piece volumes will also be suitable in broader aspects of the present invention.

Figure 3:
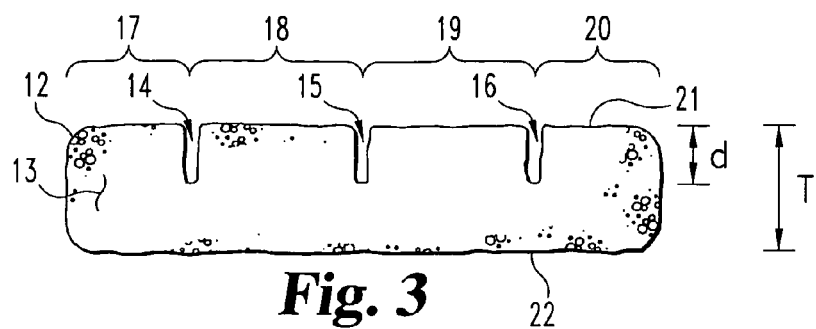
FIG. 3 provides a cross-sectional view of the medical implant body of FIG. 1 taken along line 3-3 and viewed in the direction of the arrows.
Figure 4:
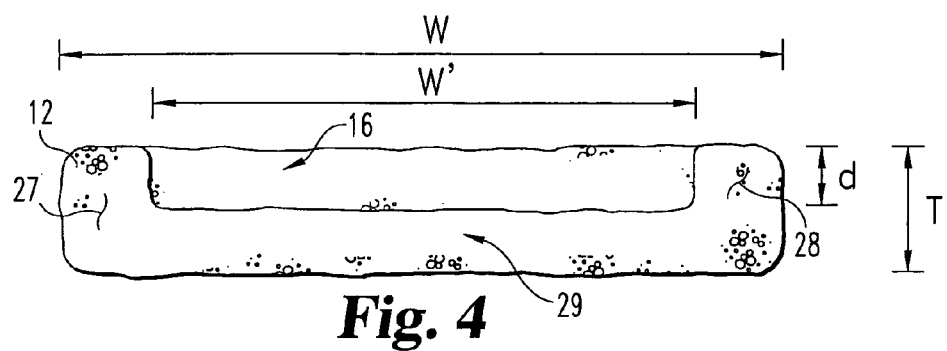
FIG. 4 provides a cross-sectional view of the medical implant body of FIG. 1 taken along line 4-4 and viewed in the direction of the arrows.

With reference now particularly to FIGS. 3 and 4, provided in FIG. 3 is a cross-sectional view taken along line 3-3 of FIG. 1 and viewed in the direction of the arrows, and provided in FIG. 4 is a cross-sectional view taken along line 4-4 of FIG. 1 and viewed in the direction of the arrows. As shown, score lines 14, 15, and 16 extend from upper surface 21 of implant body 12 partially through the thickness T of the implant body 12. These score lines in the illustrated embodiment thus extend a depth d which is thus less than the thickness T of the implant body 12. Depth d can be any suitable portion or percentage of thickness T, but depth d will generally represent 20% to 90% of thickness T, and more typically depth d will represent about 30% to about 80% of thickness T. In certain forms of the invention, depth d will range from about 40% to about 60% of thickness T.

The score lines 14, 15, and 16 also extend only partially across the width W of the implant body 12. In this manner, peripheral portions 27 and 28 will be provided at or near the periphery of implant body 12 and can serve to reinforce the overall integrity of implant body 12, for example relative to that integrity which would exist should score lines 14, 15, and 16 extend completely across the width W of implant body 12. Thus, peripheral portions 27 and 28 are relatively thicker than portion 29 in the region in which the score line 16 extends. It will be understood that similar structures and features will exist for other score lines such as 14 and 15.

Figure 5:
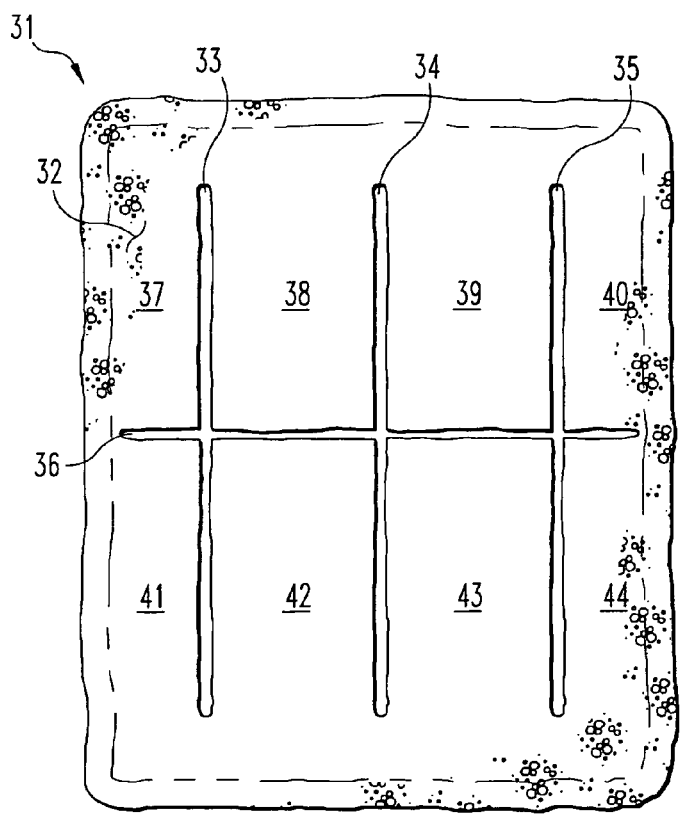
FIG. 5 provides a top view of an alternative medical implant body of the present invention.

With reference now to FIG. 5, shown is an alternative medical implant device 31 of the present invention. Device 31 includes an implant body 32 that includes a first set of score lines 33, 34, and 35 extending in a first direction along the implant body 32, as well as a score line 36 extending in a second direction transverse to that of score lines 33, 34, and 35. In the illustrated embodiment, score line 36 intersects score lines 33, 34, and 35 and is substantially perpendicular thereto. In this fashion, implant body 32 is separable in two dimensions, into a potential total of 8 individual pieces 37-44. It will be understood that in other embodiments, score line 36 would not necessarily intersect score lines 33, 34, and 35. Rather, each of score lines 33, 34, and 35 could replaced by separate score lines occurring on either side of score line 36 yet not intersecting therewith. These and other modifications in the illustrated configurations will readily occur to those skilled in the art, and are contemplated as forming a part of the present invention.

Figure 6:
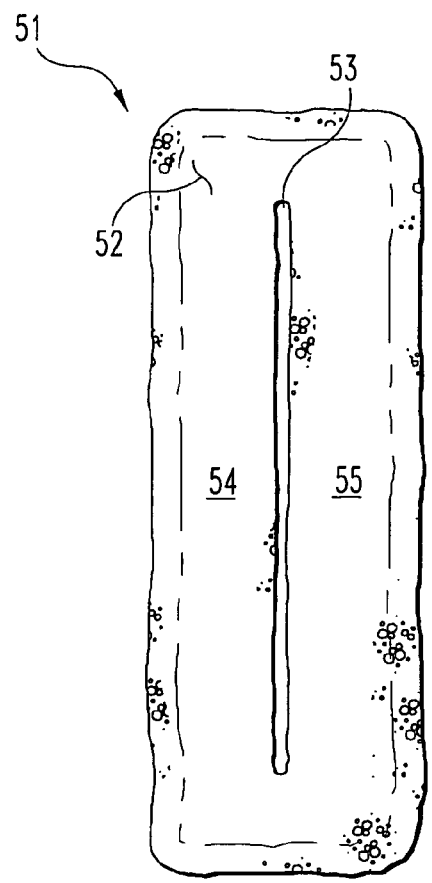
FIG. 6 provides a top view of another alternative medical implant body of the present invention.

With reference now to FIG. 6, shown is an alternative medical device 51 of the present invention including an implant body 52 and a single score line 53 rendering the body 52 separable into implant body portions 54 and 55.

Figure 7:
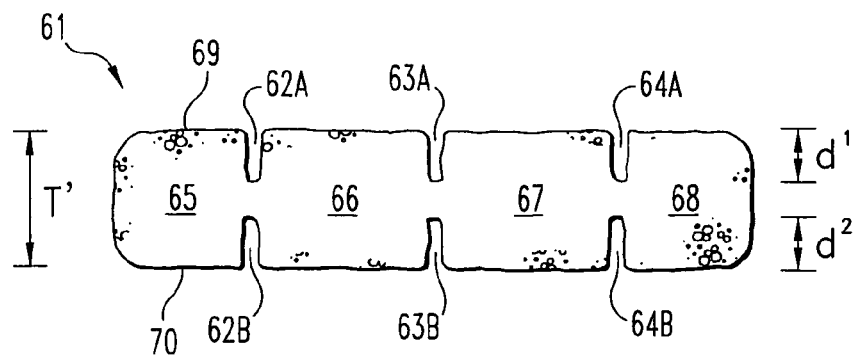
FIG. 7 provides a cross-sectional view of a medical implant body of the present invention showing an alternative score line feature.

Shown in FIG. 7 is a cross-sectional view of a medical device 61 that is similar in all respects to the medical device 11 of FIGS. 1-4, except as follows. Instead of score lines 14, 15, and 16, in the medical device 11 which extend from a single surface 21 of the implant body 12, implant body 61 includes pairs of corresponding score lines 62A and 62B, 63A and 63B, and 64A and 64B, which are aligned and which extend from opposite surfaces 69 and 70 of implant device 61. The oppositely faced score lines extend generally toward one another from the opposite surfaces 69 and 70, but do not meet. Thus, a central or intermediate amount of material separates the score lines in the score line pairs. In this manner, an alternative device 61 is provided which separates the implant body into 4 pieces, 65, 66, 67, and 68. The score lines 62A, 63A, and 64A, extend from surface 69 to a depth $d^1$, and the score lines 62B, 63B, and 64B extend from the surface 70 to a depth $d^2$, wherein $d^1+d^2$ represents a value smaller than the overall thickness $T^1$ defined between surfaces 69 and 70. In typical embodiments, $d^1+d^2$ will represent from 20% to 80% of thickness $T^1$ defined between surfaces 69 and 70, more typically in the range of about 30% to about 80%, and in certain forms of the invention from about 40% to about 60%.

Turning now to a discussion of implant materials that may be utilized in medical devices of the invention, a wide variety of biocompatible and preferably also bioresorbable materials are available. For medical devices of the invention configured to support or promote the growth of hard tissues such as bone, these materials will desirably impart osteoconductive and/or osteoinductive character to the implant body. In one embodiment, the implant body comprises a fibrous sponge.

In this regard, in certain advantageous embodiments of the invention, implants of the invention include a first implant material having an organic carrier material and a mineral-containing material. The organic carrier material can have any suitable form, and can for instance provide a resorbable matrix. Such a matrix will beneficially include a porous or non-porous polymeric matrix that can be formed with collagen or another biopolymer and/or a synthetic polymer.

A wide variety of collagen materials are suitable for use as organic carrier materials in the invention. Naturally occurring collagens may be subclassified into several different types depending on their amino acid sequence, carbohydrate content and presence or absence of disulfide cross-links. Types I and III collagen are two of the most common subtypes of collagen. Type I collagen is present in skin, tendon and bone whereas Type III collagen is found primarily in skin. The collagen in the implant material of the invention may be obtained from skin, bone, tendon, cartilage, or other natural or synthetic sources, and purified by methods known in the art. Alternatively, the collagen may be purchased commercially. The implant composition of the present invention desirably includes Type I bovine collagen.

The collagen of the matrix can further be atelopeptide collagen and/or telopeptide collagen. Moreover, both non-fibrillar and fibrillar collagen may be used. Non-fibrillar collagen is collagen that has been solubilized and has not been reconstituted into its native fibrillar form.

As noted above, the organic carrier used in an implant material may also include other natural or synthetic polymeric materials, in addition to or as an alternative to collagen. For example, the organic carrier may comprise gelatin (e.g. foamed gelatin), or resorbable synthetic polymers such as polylactic acid polymers, polyglycolic acid polymers, or copolymers thereof. Other natural and synthetic polymers are also known for use in biocompatible resorbable matrix and other carrier materials, and can be used in the invention.

The biocompatible implant material also includes a natural and/or synthetic mineral component in certain preferred forms of the invention. For example, the mineral component can be provided by a particulate mineral material, including either powder form or larger particulate mineral materials such as granular materials. In certain embodiments, the particulate mineral component is effective in providing a scaffold for bone ingrowth as the resorbable matrix material is resorbed. The mineral material may for example include bone, especially cortical bone, or a synthetic bioceramic such as a biocompatible calcium phosphate ceramic. Illustrative ceramics for these purposes include tricalcium phosphate, hydroxyapatite, and biphasic calcium phosphate. These mineral components may be purchased commercially or obtained or synthesized by methods known in the art. For instance, a granulated mineral material for use in the invention may be made as described in International Publication No. WO2004054633 of SDGI Holdings, Inc., published Jul. 1, 2004 and entitled Bone Substitute Material. A commercial granulated material suitable for use in the invention is available as Mastergraft™ ceramic granules (Medtronic Sofamor Danek, Inc., Memphis, Tenn., USA), which are composed of biphasic calcium phosphate. Desirably, when used, biphasic calcium phosphate will have a tricalcium phosphate to hydroxyapatite weight ratio of about 50:50 to about 95:5, more preferably about 70:30 to about 95:5, even more preferably about 80:20 to about 90:10, and most preferably about 85:15.

The implant material used to form implant bodies of the invention can include an amount of mineral that will provide a scaffold effective to remain in the patient for a period of time sufficient for the formation of osteoid in the void for which bone growth is desired. Typically, this period of time will be about 6 to about 8 weeks, although longer or shorter periods may also occur in particular situations. The desired level of mineral present in the implant composition may also depend upon whether any bone morphogenic proteion (BMP) or other osteogenic substance is present, as well as the level and activity of the BMP or other osteogenic protein in the composition. Generally, the higher the amount and/or activity of the osteogenic protein, the greater the content of the mineral required to provide a long-lasting scaffold for bone growth.

In certain forms of the invention, the particulate mineral: organic carrier weight ratio of the implant material will be at least about 4:1, more typically at least about 10:1. In highly mineralized implants, the particulate mineral will constitute at least about 95% by weight of the implant material. For example, highly effective first implant materials are provided wherein they comprise about 97% to about 99% by weight particulate mineral and about 1% to about 3% of the collagen or other organic carrier (desirably matrix forming) material. Moreover, the mineral component in certain embodiments has an average particle size of at least about 0.5 mm, more preferably about 0.5 mm to about 5 mm, and most preferably about 1 mm to about 3 mm.

Other biocompatible and preferably bioresorbable materials can be used in implant bodies of the invention. Desirable materials for use will have an osteoconductive or osteoinductive character. As one example, demineralized bone matrix (DBM)) may be used as an implant material for bone growth, alone or in combination with mineral materials or other organic carrier materials as discussed above.

Implants of the invention can incorporate an osteogenic protein carried by the implant material, for example received upon and/or within the implant material. For example, as noted above, the osteogenic protein can be a BMP. Recombinant human BMPs can be used, and may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. The osteogenic protein may be isolated from tissue sources such as bone. Methods for isolating BMP from bone are described, for example, in U.S. Pat. No. 4,294,753 to Urist and Urist et al., PNAS 371, 1984.

In some embodiments, the osteogenic protein will include a pair of polypeptides having amino acid sequences each comprising a sequence that shares a defined relationship with an amino acid sequence of a reference morphogenic protein. Desirable osteogenic polypeptides for use in the present invention have an amino acid sequence that shares a defined relationship with a sequence present in osteogenically active human BMP-2 (SEQ ID NO: 2; see also National Center for Biotechnology Information (NCBI) Accession No. P12643), osteogenically active human BMP-4 (SEQ ID NO: 4; see also NCBI Accession No. P12644), osteogenically active human BMP-6 (SEQ ID NO: 6; see also NCBI Accession No. P22004), or osteogenically active human BMP-7 (SEQ ID NO: 8; see also NCBI Accession No. P18075). However, any one or more of the naturally occurring or biosynthetic sequences disclosed herein similarly could be used as a reference sequence. Polypeptides in a dimeric protein with osteogenic activity can each comprise a sequence that corresponds to a reference sequence or that is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differs from the corresponding residue of a reference sequence, e.g., the C-terminal cysteine domain (also referred to herein as the conserved cysteine skeleton) of human BMP-2, provided that this difference does not destroy bone morphogenic activity. Conservative substitutions of corresponding amino acids in the reference sequence may be used. Amino acid residues that are conservative substitutions for corresponding residues in a reference sequence are those that are physically or functionally similar to the corresponding reference residues, e.g., that have similar size, shape, electric charge, chemical properties including the ability to form covalent or hydrogen bonds, or the like. Common conservative substitutions are those fulfilling the criteria defined for an accepted point mutation in Dayhoff et al. (1978), 5 Atlas of Protein Sequence and Structure, Suppl. 3, ch. 22 (pp. 354-352), Natl. Biomed. Res. Found., Washington, D.C. 20007.

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The term "conservative variation" also includes the use of a substituted amino acid in place of an unsubstituted parent amino acid provided that antibodies raised to the substituted polypeptide also immunoreact with the unsubstituted polypeptide.

As described above, particularly useful sequences for the present invention include those comprising the sequences for BMP-2 or BMP-4 (see WO88/00205, U.S. Pat. No. 5,013,649 and WO91/18098), BMP6 (see WO90/11366, PCT/US90/01630), and BMP-7 (also referred to as OP1, see U.S. Pat. No. 5,011,691 and Oppermann et al.), and functionally equivalent sequences thereto.

Publications disclosing these sequences, as well as their chemical and physical properties, include: BMP-2 and BMP-4: WO88/00205, Wozney et al. (1988) Science 242:1528-1534); BMP-7 (OP-1): U.S. Pat. No. 5,011,691, U.S. Pat. No. 5,266,683, Ozkaynak et al. (1990) EMBO J. 9: 2085-2093; and BMP-6: Celeste et al. (1991) PNAS 87: 9843-9847. Recombinant human BMP-2 (rhBMP-2), recombinant human BMP-4 (rhBMP-4), recombinant human BMP-6, recombinant human BMP-7 (rhBMP-7) or heterodimers thereof, may be used to particular advantage.

In other embodiments, useful proteins include biologically active biosynthetic constructs, including novel biosynthetic morphogenic proteins and chimeric proteins designed using sequences from two or more known morphogens.

In certain embodiments, bone morphogenic proteins useful in aspects of the invention include those in which the amino acid sequences comprise a sequence sharing at least 70% amino acid sequence homology or "similarity", and preferably 80% homology or similarity, with a reference morphogenic protein selected from the foregoing naturally occurring proteins. Preferably, the reference protein is human BMP-2, human BMP-4, human BMP-6, or human BMP-7, and the reference sequence thereof is the C-terminal cysteine domain present in osteogenically active forms of these proteins. A polypeptide suspected of being functionally equivalent to a reference morphogen polypeptide can be aligned therewith using the method of Needleman, et al. (1970) J. Mol. Biol. 48:443-453, implemented conveniently by computer programs such as the Align program (DNAstar, Inc.). Internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a currently preferred embodiment, the reference sequence is BMP-2. Bone morphogenic proteins useful herein accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins, including those set forth and identified above. Certain particularly preferred morphogenic polypeptides share at least 60% amino acid identity with the preferred reference sequence of human BMP-2, still more preferably at least 80% amino acid identity therewith.

In still other embodiments, useful osteogenically active proteins have polypeptide chains with amino acid sequences comprising a sequence encoded by a nucleic acid that hybridizes, under any or all of low, medium or high stringency hybridization conditions, to DNA or RNA encoding reference morphogen sequences, e.g., C-terminal sequences defining the conserved seven cysteine domains of BMP-2 (SEQ. ID NO. 1; see also NCBI Accession No. NM001200), BMP-4 (SEQ. ID NO. 3; see also NCBI Accession Nos. NM001202; NM130850; NM130851), BMP-6 (SEQ. ID NO. 5; see also NCBI Accession No. 001718) or BMP-7 (SEQ. ID NO. 7; see also NCBI Accession No. 001719), and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984): Nucleic Acid Hybridization (B. D. Hames & S. J. Higgins eds. 1984); and B. Perbal, A Practical Guide To Molecular Cloning (1984).

Proteins useful in the present invention generally are dimeric proteins comprising a folded pair of polypeptides. Such morphogenic proteins are inactive when reduced, but are active as oxidized homodimers and when oxidized in combination with others of this invention to produce heterodimers. Thus, members of a folded pair of morphogenic polypeptides in a morphogenically active protein can be selected independently from any of the specific polypeptides mentioned above.

Bone morphogenic proteins useful in the invention include proteins comprising any of the polypeptide chains described above, whether isolated from naturally-occurring sources, or produced by recombinant DNA or other synthetic techniques, and includes allelic and phylogenetic counterpart variants of these proteins, as well as muteins thereof, and various truncated and fusion constructs. Deletion or addition mutants also are envisioned to be active, including those that may alter the conserved C-terminal cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The bone morphogenic proteins contemplated herein can be expressed from intact or truncated cDNA or from synthetic DNAs in prokaryotic or eukaryotic host cells, and purified, cleaved, refolded, and dimerized to form morphogenically active compositions. Candidate host cells include, without limitation, prokaryotes including *E. coli*, or eukaryotes including yeast, or mammalian cells, such as CHO, COS or BSC cells. One of ordinary skill in the art will appreciate that other host cells can be used to advantage. Detailed descriptions of specific bone morphogenic proteins useful in the practice of this invention, including how to make, use and test them for osteogenic activity, are disclosed in numerous publications, including for example those referenced hereinabove. Additional osteogenic proteins that may be used in aspects of the present invention are included in the group of osteogenic proteins identified in U.S. patent application Ser. No. 09/045,331 filed Mar. 20, 1998, published Aug. 23, 2001 as US 20010016646 A1.

Thus, in view of this disclosure and the knowledge available in the art, skilled genetic engineers can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating endochondral bone morphogenesis in a mammal.

Implant bodies of the invention can be manufactured using any suitable technique. In certain forms of the invention, the implant body is molded from a suitable, moldable implant material. For example, to make one form of an implant material, a collagen or other polymer slurry may be prepared as known, and can be chilled to increase its viscosity to help suspend a particulate mineral component. A particulate mineral is dispersed into the slurry and gently mixed. After the particulate mineral component is uniformly dispersed in the slurry, the slurry is poured into sterile trays or other forms to form a single implant body or multiple implant bodies including features to form one or more separation-assist lines in each implant body, and freeze dried. The separation-assist lines can be formed, for example, by incorporating walls within the mold to form score lines as depicted in the Figures. In other illustrative embodiments, perforation lines can be formed by incorporating posts in the mold. The sheets of implant material are then removed from the freeze drier and if desired exposed to a cross-linking agent such as, for example, glutaraldehyde. The organic carrier:mineral composite material formed is desirably three-dimensionally stable but flexible, porous, and exhibits substantial resistance to compression, e.g. suffering essentially no compression under the forces normally imparted by soft tissues surrounding an implant site in contact with a bone.

In specific embodiments, the implant body of the invention can be configured to provide an implant material for use in a spinal fusion procedure, for example a posterolateral spinal fusion procedure or an interbody spinal fusion procedure. Illustratively, in a posterolateral fusion procedure, the implant body or a separable constituent portion thereof can be sized for insertion between adjacent transverse processes of a human patient, e.g. in the lumbar spine, so as to occupy the spatial volume therebetween. Implant bodies may also be configured for insertion into the interbody space between adjacent vertebral bodies, either alone or in combination with a load-bearing device such as a spinal cage or spinal spacer.

As disclosed above, the implant body of a medical device of the invention can be used in multiple fashions. In one mode, the implant body including the separation-assist line(s) can be implanted as a whole. In certain embodiments, the separation-assist line(s) can serve to increase the flexibility of an implant body formed of a flexible material. This may facilitate conformation of the overall implant body to an implant site of interest. In other modes, the implant body can be manipulated manually to separate the implant body into multiple pieces generally along the separation-assist line or lines. Such manipulation can involve any suitable method of applying force to the body to achieve separation, including for example bending, twisting, pulling, striking, or other techniques, applied one time or multiple times to separate the body into the pre-defined, multiple pieces.

Separable implant bodies can be conveniently handled by the physician or other caregiver as a whole up until near the time of implant. The caregiver may then separate the implant body and use some or all of the resulting pieces, at the same implant site or at different implant sites. In one manner of use, a caregiver can separate the implant body as necessary to achieve an appropriately sized implant piece based upon an observed defect site or fusion implant site, for example. Alternatively, the caregiver may separate the implant body in accordance with instructions provided specific to a given procedure (e.g. a fusion procedure) to be performed with the device. As one example, in a bilateral spinal fusion procedure, such as a posterolateral transverse process spinal fusion procedure, a single implant body separable into two substantially equally sized pieces can be manipulated to achieve such separation, and thereafter one of the pieces can be used on each side of the bilateral fusion procedure.

In accordance with certain aspects of the present invention, the separation-assist lines can advantageously facilitate increased accuracy in separating implant volumes intraoperatively within the sterile field. This in turn can benefit the incorporation of osteoinductive growth factor formulations or other therapeutic substances into the implant material at a known, controlled concentration. Further in this regard, the separation-assist lines of implant bodies of the present invention can serve as a guide to uniformly wetting all or portions of the implant bodies with osteogenic formulations, either before or after separation of the implant bodies into two or more pieces.

The present invention also provides medical kits including a medical implant device of the invention received within sterile packaging. Such packaging may take on any suitable form, including pouches, vials, trays, syringes, etc. Such medical kits may also include one or more other components such as osteogenic protein(s) or other active ingredient(s), aqueous liquid(s) (e.g. saline solutions), needle(s), syringe(s), tray(s), surgical instrument(s) for site access and/or delivery of the implant materials, as well as written instructions relating to the use of the inventive implant body or bodies in the kit, e.g. for bone growth or otherwise.

While the invention has been illustrated and described in detail in the foregoing description, the same is to be considered as illustrative and not restrictive in character, it being understood that only certain embodiments have been shown and described and that all changes and modifications that come within the spirit of the invention are desired to be protected. In addition, all publications cited herein are hereby incorporated by reference in their entirety as if each had been individually incorporated by reference and fully set forth.

What is claimed is:

1. A medical implant device, comprising:
a biocompatible, three-dimensional osteoconductive or osteoinductive implant body, the implant body comprising a sponge including mineral particles disposed uniformly within the sponge, said body including an upper surface, a lower surface, and side walls interconnecting the upper surface and the lower surface, wherein the implant body has a thickness of from 2 cm to 15 cm; and at least one separation-assist line defined in said implant body, said separation-assist line configured to facilitate separation of a first portion of the implant body from a second portion of the implant body by manipulating the implant body to manually break or tear the implant body along the separation-assist line into multiple separate pieces, wherein said separation-assist line comprises at least a first score line extending inwardly from a first surface of said implant body and at least a second score line extending inwardly from a second surface of said implant body, said second score line oppositely faced to and aligned with said first score line, and said first score line and second score line having a depth that comprises 20% to 60% of said thickness of the implant body and the sponge comprising fibrillar and non-fibrillar collagen and the implant comprises a plurality of said separation-assist lines extending only partially across a width of the implant body.

2. The medical implant device of claim 1, wherein said sponge includes a porous matrix comprising a synthetic or naturally occurring polymer.

3. The medical implant device of claim 1, wherein the first score line and the second score line have a thickness that comprises 20% of said thickness of the implant body.

4. The medical implant device of claim 1, wherein said mineral particles comprise biphasic calcium phosphate.

5. The medical implant device of claim 1, wherein, said separation-assist lines are configured to facilitate separation of the implant body into two to ten pieces.

6. The medical implant device of claim 5, wherein said pieces each have a volume of about 1 cc to about 50 cc.

7. The medical implant device of claim 5, wherein said implant body has a volume of about 2 cc to about 100 cc.

8. The medical implant device of claim 1, wherein said implant body is osteoconductive.

9. The medical implant device of claim 1, wherein said implant body is osteoinductive.

10. The medical implant device of claim 1, wherein the sponge comprises collagen and the weight ratio of said mineral particles to said collagen is at least 4:1.

11. The medical implant device of claim 1, wherein said collagen comprises Type I collagen.

12. The medical implant device of claim 1, wherein said implant body is formed of a flexible material having an ability to conform to an implant site at which bone growth is desired.

13. A medical implant device according to claim 1, wherein the implant further comprises peripheral portions that are thicker than the at least one separation-assist line, the peripheral portions configured to reinforce the implant.

14. A medical device suitable for implant to support or induce bone growth, the device comprising: an osteoinductive or osteoconductive implant body, said implant body defining at least one separation-assist line configured to facilitate separation of a first portion of the implant body from a second portion of the implant body into multiple separate pieces by manipulating the implant body to manually break or tear the implant body along the separation-assist line, and said implant body comprises a sponge and a mineral disposed uniformly throughout the sponge, and the implant body has a thickness of from 2 cm to 15 cm, and wherein said separation-assist line comprises at least a first score line extending inwardly from a first surface of said implant body and at least a second score line extending inwardly from a second surface of said implant body, said second score line oppositely faced to and aligned with said first score line, and said first score line and second score line having a depth that comprises 20% to 60% of said thickness of the implant body and the sponge comprises fibrillar and non-fibrillar collagen and the implant comprises a plurality of said separation-assist lines extending only partially across a width of the implant body.

15. The medical device of claim 14, wherein said implant body comprises a resorbable flexible material having an ability to conform to an implant site at which bone growth is desired.

16. The medical device of claim 15, wherein the first score line and the second score line have a depth that comprises 20% of the thickness of the implant body.

17. A medical product, comprising: an osteoinductive or osteoconductive implant body, said implant body defining at least one separation-assist line configured to facilitate separation of a first portion of the implant body from a second portion of the implant body by manipulating the implant body to manually break or tear the implant body along the separation-assist line into multiple separate pieces; and packaging enclosing said implant body in a sterile condition, wherein said implant body comprises a sponge and a mineral disposed uniformly throughout the sponge and said implant body has a thickness of from 2 cm to 15 cm and wherein said separation-assist line comprises at least a first score line extending inwardly from a first surface of said implant body and at least a second score line extending inwardly from a second surface of said implant body, said second score line opposite faced to and aligned with said first score line, and said first score line and second score line having a depth that comprises 20% to 60% of said thickness of the implant body and the sponge comprises fibrillar and non-fibrillar collagen and the implant comprises a plurality of said separation-assist lines extending only partially across a width of the implant body.

18. The medical product of claim 17, wherein said implant body comprises a natural or synthetic polymer, wherein said implant body is formed of a flexible material having an ability to conform to an implant site at which bone growth is desired, and further wherein said at least one separation-assist line increases the flexibility of the implant body.

* * * * *

SEQUENCE LISTING

<160> NUMBER OF SEQ ID NOS: 8

<210> SEQ ID NO 1
<211> LENGTH: 1547
<212> TYPE: DNA
<213> ORGANISM: Homo sapiens
<220> FEATURE:

```
<221> NAME/KEY: CDS
<222> LOCATION: (324)..(1514)

<400> SEQUENCE: 1
ggggacttct tgaacttgca gggagaataa cttgcgcacc ccactttgcg ccggtgcctt      60
tgccccagcg gagcctgctt cgccatctcc gagccccacc gcccctccac tcctcggcct     120
tgcccgacac tgagacgctg ttcccagcgt gaaagagag actgcgcggc cggcaccccgg    180 gagaaggagg aggcaaagaa aaggaacgga cattcggtcc ttgcgccagg tcctttgacc    240 agagttttc catgtggacg ctctttcaat ggacgtgtcc ccgcgtgctt cttagacgga     300
ctgcggtctc ctaaaggtcg acc atg gtg gcc ggg acc cgc tgt ctt cta gcg   353
                          Met Val Ala Gly Thr Arg Cys Leu Leu Ala
                           1               5                  10 ttg ctg ctt ccc cag gtc ctc ctg ggc ggc gcg gct ggc ctc gtt ccg      401
Leu Leu Leu Pro Gln Val Leu Leu Gly Gly Ala Ala Gly Leu Val Pro
             15                  20                  25 gag ctg ggc cgc agg aag ttc gcg gcg gcg tcg tcg ggc cgc ccc tca      449
Glu Leu Gly Arg Arg Lys Phe Ala Ala Ala Ser Ser Gly Arg Pro Ser
         30                  35                  40 tcc cag ccc tct gac gag gtc ctg agc gag ttc gag ttg cgg ctg ctc      497
Ser Gln Pro Ser Asp Glu Val Leu Ser Glu Phe Glu Leu Arg Leu Leu
     45                  50                  55 agc atg ttc ggc ctg aaa cag aga ccc acc ccc agc agg gac gcc gtg      545
Ser Met Phe Gly Leu Lys Gln Arg Pro Thr Pro Ser Arg Asp Ala Val
 60                  65                  70 gtg ccc ccc tac atg cta gac ctg tat cgc agg cac tca ggt cag ccg      593
Val Pro Pro Tyr Met Leu Asp Leu Tyr Arg Arg His Ser Gly Gln Pro
75                  80                  85                  90 ggc tca ccc gcc cca gac cac cgg ttg gag agg gca gcc agc cga gcc      641
Gly Ser Pro Ala Pro Asp His Arg Leu Glu Arg Ala Ala Ser Arg Ala
                 95                 100                 105 aac act gtg cgc agc ttc cac cat gaa gaa tct ttg gaa gaa cta cca      689
Asn Thr Val Arg Ser Phe His His Glu Glu Ser Leu Glu Glu Leu Pro
            110                 115                 120 gaa acg agt ggg aaa aca acc cgg aga ttc ttc ttt aat tta agt tct      737
Glu Thr Ser Gly Lys Thr Thr Arg Arg Phe Phe Phe Asn Leu Ser Ser
        125                 130                 135 atc ccc acg gag gag ttt atc acc tca gca gag ctt cag gtt ttc cga      785
Ile Pro Thr Glu Glu Phe Ile Thr Ser Ala Glu Leu Gln Val Phe Arg
    140                 145                 150 gaa cag atg caa gat gct tta gga aac aat agc agt ttc cat cac cga      833
Glu Gln Met Gln Asp Ala Leu Gly Asn Asn Ser Ser Phe His His Arg
155                 160                 165                 170 att aat att tat gaa atc ata aaa cct gca aca gcc aac tcg aaa ttc      881
Ile Asn Ile Tyr Glu Ile Ile Lys Pro Ala Thr Ala Asn Ser Lys Phe
                175                 180                 185 ccc gtg acc aga ctt ttg gac acc agg ttg gtg aat cag aat gca agc      929
Pro Val Thr Arg Leu Leu Asp Thr Arg Leu Val Asn Gln Asn Ala Ser
            190                 195                 200 agg tgg gaa agt ttt gat gtc acc ccc gct gtg atg cgg tgg act gca      977
Arg Trp Glu Ser Phe Asp Val Thr Pro Ala Val Met Arg Trp Thr Ala
        205                 210                 215 cag gga cac gcc aac cat gga ttc gtg gtg gaa gtg gcc cac ttg gag     1025
Gln Gly His Ala Asn His Gly Phe Val Val Glu Val Ala His Leu Glu
    220                 225                 230 gag aaa caa ggt gtc tcc aag aga cat gtt agg ata agc agg tct ttg     1073
Glu Lys Gln Gly Val Ser Lys Arg His Val Arg Ile Ser Arg Ser Leu
235                 240                 245                 250 cac caa gat gaa cac agc tgg tca cag ata agg cca ttg cta gta act     1121
```

```
His Gln Asp Glu His Ser Trp Ser Gln Ile Arg Pro Leu Leu Val Thr
                255                 260                 265 ttt ggc cat gat gga aaa ggg cat cct ctc cac aaa aga gaa aaa cgt    1169
Phe Gly His Asp Gly Lys Gly His Pro Leu His Lys Arg Glu Lys Arg
                270                 275                 280 caa gcc aaa cac aaa cag cgg aaa cgc ctt aag tcc agc tgt aag aga    1217
Gln Ala Lys His Lys Gln Arg Lys Arg Leu Lys Ser Ser Cys Lys Arg
                285                 290                 295 cac cct ttg tac gtg gac ttc agt gac gtg ggg tgg aat gac tgg att    1265
His Pro Leu Tyr Val Asp Phe Ser Asp Val Gly Trp Asn Asp Trp Ile
            300                 305                 310 gtg gct ccc ccg ggg tat cac gcc ttt tac tgc cac gga gaa tgc cct    1313
Val Ala Pro Pro Gly Tyr His Ala Phe Tyr Cys His Gly Glu Cys Pro
315             320                 325                 330 ttt cct ctg gct gat cat ctg aac tcc act aat cat gcc att gtt cag    1361
Phe Pro Leu Ala Asp His Leu Asn Ser Thr Asn His Ala Ile Val Gln
                335                 340                 345 acg ttg gtc aac tct gtt aac tct aag att cct aag gca tgc tgt gtc    1409
Thr Leu Val Asn Ser Val Asn Ser Lys Ile Pro Lys Ala Cys Cys Val
                350                 355                 360 ccg aca gaa ctc agt gct atc tcg atg ctg tac ctt gac gag aat gaa    1457
Pro Thr Glu Leu Ser Ala Ile Ser Met Leu Tyr Leu Asp Glu Asn Glu
                365                 370                 375 aag gtt gta tta aag aac tat cag gac atg gtt gtg gag ggt tgt ggg    1505
Lys Val Val Leu Lys Asn Tyr Gln Asp Met Val Val Glu Gly Cys Gly
380                 385                 390 tgt cgc tag tacagcaaaa ttaaatacat aaatatatat ata                   1547
Cys Arg
395

<210> SEQ ID NO 2
<211> LENGTH: 396
<212> TYPE: PRT
<213> ORGANISM: Homo sapiens

<400> SEQUENCE: 2

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
        50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175
```

-continued

```
Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 3
<211> LENGTH: 1400
<212> TYPE: DNA
<213> ORGANISM: Homo sapiens
<220> FEATURE:
<221> NAME/KEY: CDS
<222> LOCATION: (102)..(1310)

<400> SEQUENCE: 3
gaggcactgc ttggaagcaa ttgtagagca atacagctct tgacaaactc gtgtcgaaca      60
tcagtgactg ttgaagggaa tgaggcaaac atatctacgg a atg ctg atg gtc gtt    116
                                              Met Leu Met Val Val
                                                1               5 tta tta tgc caa gtc ctg cta gga ggc gcg agc cat gct agt ttg ata      164
Leu Leu Cys Gln Val Leu Leu Gly Gly Ala Ser His Ala Ser Leu Ile
            10                  15                  20 cct gag acg ggg aag aaa aaa gtc gcc gag att cag ggc cac gcg gga      212
Pro Glu Thr Gly Lys Lys Lys Val Ala Glu Ile Gln Gly His Ala Gly
        25                  30                  35 gga cgc cgc tca ggg cag agc cat gag ctc ctg cgg gac ttc gag gcg      260
Gly Arg Arg Ser Gly Gln Ser His Glu Leu Leu Arg Asp Phe Glu Ala
    40                  45                  50 aca ctt ctg cag atg ttt ggg ctg cgc cgc ccg cag cct agc aag          308
Thr Leu Leu Gln Met Phe Gly Leu Arg Arg Arg Pro Gln Pro Ser Lys
55                  60                  65 agt gcc gtc att ccg gac tac atg cgg gat ctt tac cgg ctt cag tct      356
Ser Ala Val Ile Pro Asp Tyr Met Arg Asp Leu Tyr Arg Leu Gln Ser
70                  75                  80                  85 ggg gag gag gag gaa gag cag atc cac agc act ggt ctt gag tat cct      404
```

```
                Gly Glu Glu Glu Glu Glu Gln Ile His Ser Thr Gly Leu Glu Tyr Pro
                            90                  95                 100 gag cgc ccg gcc agc cgg gcc aac acc gtg agg agc ttc cac cac gaa         452
Glu Arg Pro Ala Ser Arg Ala Asn Thr Val Arg Ser Phe His His Glu
            105                 110                 115 gaa cat ctg gag aac atc cca ggg acc agt gaa aac tct gct ttt cgt         500
Glu His Leu Glu Asn Ile Pro Gly Thr Ser Glu Asn Ser Ala Phe Arg
120                 125                 130 ttc ctc ttt aac ctc agc agc atc cct gag aac gag gtg atc tcc tct         548
Phe Leu Phe Asn Leu Ser Ser Ile Pro Glu Asn Glu Val Ile Ser Ser
        135                 140                 145 gca gag ctt cgg ctc ttc cgg gag cag gtg gac cag ggc cct gat tgg         596
Ala Glu Leu Arg Leu Phe Arg Glu Gln Val Asp Gln Gly Pro Asp Trp
150                 155                 160                 165 gaa agg ggc ttc cac cgt ata aac att tat gag gtt atg aag ccc cca         644
Glu Arg Gly Phe His Arg Ile Asn Ile Tyr Glu Val Met Lys Pro Pro
                170                 175                 180 gca gaa gtg gtg cct ggg cac ctc atc aca cga cta ctg gac acg aga         692
Ala Glu Val Val Pro Gly His Leu Ile Thr Arg Leu Leu Asp Thr Arg
            185                 190                 195 ctg gtc cac cac aat gtg aca cgg tgg gaa act ttt gat gtg agc cct         740
Leu Val His His Asn Val Thr Arg Trp Glu Thr Phe Asp Val Ser Pro
        200                 205                 210 gcg gtc ctt cgc tgg acc cgg gag aag cag cca aac tat ggg cta gcc         788
Ala Val Leu Arg Trp Thr Arg Glu Lys Gln Pro Asn Tyr Gly Leu Ala
215                 220                 225 att gag gtg act cac ctc cat cag act cgg acc cac cag ggc cag cat         836
Ile Glu Val Thr His Leu His Gln Thr Arg Thr His Gln Gly Gln His
230                 235                 240                 245 gtc agg att agc cga tcg tta cct caa ggg agt ggg aat tgg gcc cag         884
Val Arg Ile Ser Arg Ser Leu Pro Gln Gly Ser Gly Asn Trp Ala Gln
                250                 255                 260 ctc cgg ccc ctc ctg gtc acc ttt ggc cat gat ggc cgg ggc cat gcc         932
Leu Arg Pro Leu Leu Val Thr Phe Gly His Asp Gly Arg Gly His Ala
            265                 270                 275 ttg acc cga cgc cgg agg gcc aag cgt agc cct aag cat cac tca cag         980
Leu Thr Arg Arg Arg Ala Lys Arg Ser Pro Lys His His Ser Gln
        280                 285                 290 cgg gcc agg aag aag aat aag aac tgc cgg cgc cac tcg ctc tat gtg        1028
Arg Ala Arg Lys Lys Asn Lys Asn Cys Arg Arg His Ser Leu Tyr Val
295                 300                 305 gac ttc agc gat gtg ggc tgg aat gac tgg att gtg gcc cca cca ggc        1076
Asp Phe Ser Asp Val Gly Trp Asn Asp Trp Ile Val Ala Pro Pro Gly
310                 315                 320                 325 tac cag gcc ttc tac tgc cat ggg gac tgc ccc ttt cca ctg gct gac        1124
Tyr Gln Ala Phe Tyr Cys His Gly Asp Cys Pro Phe Pro Leu Ala Asp
                330                 335                 340 cac ctc aac tca acc aac cat gcc att gtg cag acc ctg gtc aat tct        1172
His Leu Asn Ser Thr Asn His Ala Ile Val Gln Thr Leu Val Asn Ser
            345                 350                 355 gtc aat tcc agt atc ccc aaa gcc tgt tgt gtg ccc act gaa ctg agt        1220
Val Asn Ser Ser Ile Pro Lys Ala Cys Cys Val Pro Thr Glu Leu Ser
        360                 365                 370 gcc atc tcc atg ctg tac ctg gat gag tat gat aag gtg gta ctg aaa        1268
Ala Ile Ser Met Leu Tyr Leu Asp Glu Tyr Asp Lys Val Val Leu Lys
375                 380                 385 aat tat cag gag atg gta gta gag gga tgt ggg tgc cgc tga                1310
Asn Tyr Gln Glu Met Val Val Glu Gly Cys Gly Cys Arg
                390                 395                 400 gatcaggcag tccttgagga tagacagata tacacaccac acacacacac cacatacacc      1370
```
acacacacac gttcccatcc actcacccac                                          1400

<210> SEQ ID NO 4
<211> LENGTH: 402
<212> TYPE: PRT
<213> ORGANISM: Homo sapiens

<400> SEQUENCE: 4

Met Leu Met Val Val Leu Leu Cys Gln Val Leu Leu Gly Gly Ala Ser
1               5                   10                  15

His Ala Ser Leu Ile Pro Glu Thr Gly Lys Lys Val Ala Glu Ile
            20                  25                  30

Gln Gly His Ala Gly Gly Arg Arg Ser Gly Gln Ser His Glu Leu Leu
            35                  40                  45

Arg Asp Phe Glu Ala Thr Leu Leu Gln Met Phe Gly Leu Arg Arg Arg
        50                  55                  60

Pro Gln Pro Ser Lys Ser Ala Val Ile Pro Asp Tyr Met Arg Asp Leu
65                  70                  75                  80

Tyr Arg Leu Gln Ser Gly Glu Glu Glu Glu Gln Ile His Ser Thr
                85                  90                  95

Gly Leu Glu Tyr Pro Glu Arg Pro Ala Ser Arg Ala Asn Thr Val Arg
            100                 105                 110

Ser Phe His His Glu Glu His Leu Glu Asn Ile Pro Gly Thr Ser Glu
            115                 120                 125

Asn Ser Ala Phe Arg Phe Leu Phe Asn Leu Ser Ser Ile Pro Glu Asn
        130                 135                 140

Glu Val Ile Ser Ser Ala Glu Leu Arg Leu Phe Arg Glu Gln Val Asp
145                 150                 155                 160

Gln Gly Pro Asp Trp Glu Arg Gly Phe His Arg Ile Asn Ile Tyr Glu
                165                 170                 175

Val Met Lys Pro Pro Ala Glu Val Val Pro Gly His Leu Ile Thr Arg
            180                 185                 190

Leu Leu Asp Thr Arg Leu Val His His Asn Val Thr Arg Trp Glu Thr
            195                 200                 205

Phe Asp Val Ser Pro Ala Val Leu Arg Trp Thr Arg Glu Lys Gln Pro
        210                 215                 220

Asn Tyr Gly Leu Ala Ile Glu Val Thr His Leu His Gln Thr Arg Thr
225                 230                 235                 240

His Gln Gly Gln His Val Arg Ile Ser Arg Ser Leu Pro Gln Gly Ser
                245                 250                 255

Gly Asn Trp Ala Gln Leu Arg Pro Leu Leu Val Thr Phe Gly His Asp
            260                 265                 270

Gly Arg Gly His Ala Leu Thr Arg Arg Arg Arg Ala Lys Arg Ser Pro
            275                 280                 285

Lys His His Ser Gln Arg Ala Arg Lys Lys Asn Lys Asn Cys Arg Arg
        290                 295                 300

His Ser Leu Tyr Val Asp Phe Ser Asp Val Gly Trp Asn Asp Trp Ile
305                 310                 315                 320

Val Ala Pro Pro Gly Tyr Gln Ala Phe Tyr Cys His Gly Asp Cys Pro
                325                 330                 335

Phe Pro Leu Ala Asp His Leu Asn Ser Thr Asn His Ala Ile Val Gln
            340                 345                 350

Thr Leu Val Asn Ser Val Asn Ser Ser Ile Pro Lys Ala Cys Cys Val
            355                 360                 365

-continued

```
Pro Thr Glu Leu Ser Ala Ile Ser Met Leu Tyr Leu Asp Glu Tyr Asp
    370                 375                 380

Lys Val Val Leu Lys Asn Tyr Gln Glu Met Val Val Glu Gly Cys Gly
385                 390                 395                 400

Cys Arg
```

<210> SEQ ID NO 5
<211> LENGTH: 2943
<212> TYPE: DNA
<213> ORGANISM: Homo sapiens
<220> FEATURE:
<221> NAME/KEY: CDS
<222> LOCATION: (180)..(1721)

<400> SEQUENCE: 5

| | | |
|---|---|---|
| gcaactgggg gcgccccgga cgaccatgag agataaggac tgagggccag gaagggaag | 60 |
| cgagcccgcc gagaggtggc ggggactgct cacgccaagg gccacagcgg ccgcgctccg | 120 |
| gcctcgctcc gccgctccac gcctcgcggg atccgcgggg gcagcccggc cgggcgggg | 179 |

```
atg ccg ggg ctg ggg cgg agg gcg cag tgg ctg tgc tgg tgg tgg ggg    227
Met Pro Gly Leu Gly Arg Arg Ala Gln Trp Leu Cys Trp Trp Trp Gly
1               5                   10                  15 ctg ctg tgc agc tgc tgc ggg ccc ccg ccg ctg cgg ccg ccc ttg ccc    275
Leu Leu Cys Ser Cys Cys Gly Pro Pro Pro Leu Arg Pro Pro Leu Pro
                20                  25                  30 gct gcc gcg gcc gcc gcc ggg ggg cag ctg ctg ggg gac ggc ggg        323
Ala Ala Ala Ala Ala Ala Gly Gly Gln Leu Leu Gly Asp Gly Gly
                35                  40                  45 agc ccc ggc cgc acg gag cag ccg ccg ccg tcg ccg cag tcc tcc tcg    371
Ser Pro Gly Arg Thr Glu Gln Pro Pro Pro Ser Pro Gln Ser Ser Ser
    50                  55                  60 ggc ttc ctg tac cgg cgg ctc aag acg cag gag aag cgg gag atg cag    419
Gly Phe Leu Tyr Arg Arg Leu Lys Thr Gln Glu Lys Arg Glu Met Gln
65              70                  75                  80 aag gag atc ttg tcg gtg ctg ggg ctc ccg cac cgg ccc cgg ccc ctg    467
Lys Glu Ile Leu Ser Val Leu Gly Leu Pro His Arg Pro Arg Pro Leu
                85                  90                  95 cac ggc ctc caa cag ccg cag ccc ccg gcg ctc cgg cag cag gag gag    515
His Gly Leu Gln Gln Pro Gln Pro Pro Ala Leu Arg Gln Gln Glu Glu
                100                 105                 110 cag cag cag cag cag cag ctg cct cgc gga gag ccc cct ccc ggg cga    563
Gln Gln Gln Gln Gln Gln Leu Pro Arg Gly Glu Pro Pro Pro Gly Arg
            115                 120                 125 ctg aag tcc gcg ccc ctc ttc atg ctg gat ctg tac aac gcc ctg tcc    611
Leu Lys Ser Ala Pro Leu Phe Met Leu Asp Leu Tyr Asn Ala Leu Ser
    130                 135                 140 gcc gac aac gac gag gac ggg gcg tcg gag ggg gag agg cag cag tcc    659
Ala Asp Asn Asp Glu Asp Gly Ala Ser Glu Gly Glu Arg Gln Gln Ser
145                 150                 155                 160 tgg ccc cac gaa gca gcc agc tcg tcc cag cgt cgg cag ccg ccc ccg    707
Trp Pro His Glu Ala Ala Ser Ser Ser Gln Arg Arg Gln Pro Pro Pro
                165                 170                 175 ggc gcc gcg cac ccg ctc aac cgc aag agc ctt ctg gcc ccc gga tct    755
Gly Ala Ala His Pro Leu Asn Arg Lys Ser Leu Leu Ala Pro Gly Ser
                180                 185                 190 ggc agc ggc ggc gcg tcc cca ctg acc agc gcg cag gac agc gcc ttc    803
Gly Ser Gly Gly Ala Ser Pro Leu Thr Ser Ala Gln Asp Ser Ala Phe
            195                 200                 205 ctc aac gac gcg gac atg gtc atg agc ttt gtg aac ctg gtg gag tac    851
Leu Asn Asp Ala Asp Met Val Met Ser Phe Val Asn Leu Val Glu Tyr
    210                 215                 220
```

```
gac aag gag ttc tcc cct cgt cag cga cac cac aaa gag ttc aag ttc      899
Asp Lys Glu Phe Ser Pro Arg Gln Arg His His Lys Glu Phe Lys Phe
225                 230                 235                 240 aac tta tcc cag att cct gag ggt gag gtg gtg acg gct gca gaa ttc      947
Asn Leu Ser Gln Ile Pro Glu Gly Glu Val Val Thr Ala Ala Glu Phe
                245                 250                 255 cgc atc tac aag gac tgt gtt atg ggg agt ttt aaa aac caa act ttt      995
Arg Ile Tyr Lys Asp Cys Val Met Gly Ser Phe Lys Asn Gln Thr Phe
            260                 265                 270 ctt atc agc att tat caa gtc tta cag gag cat cag cac aga gac tct     1043
Leu Ile Ser Ile Tyr Gln Val Leu Gln Glu His Gln His Arg Asp Ser
        275                 280                 285 gac ctg ttt ttg ttg gac acc cgt gta gta tgg gcc tca gaa gaa ggc     1091
Asp Leu Phe Leu Leu Asp Thr Arg Val Val Trp Ala Ser Glu Glu Gly
    290                 295                 300 tgg ctg gaa ttt gac atc acg gcc act agc aat ctg tgg gtt gtg act     1139
Trp Leu Glu Phe Asp Ile Thr Ala Thr Ser Asn Leu Trp Val Val Thr
305                 310                 315                 320 cca cag cat aac atg ggg ctt cag ctg agc gtg gtg aca agg gat gga     1187
Pro Gln His Asn Met Gly Leu Gln Leu Ser Val Val Thr Arg Asp Gly
                325                 330                 335 gtc cac gtc cac ccc cga gcc gca ggc ctg gtg ggc aga gac ggc cct     1235
Val His Val His Pro Arg Ala Ala Gly Leu Val Gly Arg Asp Gly Pro
            340                 345                 350 tac gat aag cag ccc ttc atg gtg gct ttc ttc aaa gtg agt gag gtc     1283
Tyr Asp Lys Gln Pro Phe Met Val Ala Phe Phe Lys Val Ser Glu Val
        355                 360                 365 cac gtg cgc acc acc agg tca gcc tcc agc cgg cgc cga caa cag agt     1331
His Val Arg Thr Thr Arg Ser Ala Ser Ser Arg Arg Arg Gln Gln Ser
    370                 375                 380 cgt aat cgc tct acc cag tcc cag gac gtg gcg cgg gtc tcc agt gct     1379
Arg Asn Arg Ser Thr Gln Ser Gln Asp Val Ala Arg Val Ser Ser Ala
385                 390                 395                 400 tca gat tac aac agc agt gaa ttg aaa aca gcc tgc agg aag cat gag     1427
Ser Asp Tyr Asn Ser Ser Glu Leu Lys Thr Ala Cys Arg Lys His Glu
                405                 410                 415 ctg tat gtg agt ttc caa gac ctg gga tgg cag gac tgg atc att gca     1475
Leu Tyr Val Ser Phe Gln Asp Leu Gly Trp Gln Asp Trp Ile Ile Ala
            420                 425                 430 ccc aag ggc tat gct gcc aat tac tgt gat gga gaa tgc tcc ttc cca     1523
Pro Lys Gly Tyr Ala Ala Asn Tyr Cys Asp Gly Glu Cys Ser Phe Pro
        435                 440                 445 ctc aac gca cac atg aat gca acc aac cac gcg att gtg cag acc ttg     1571
Leu Asn Ala His Met Asn Ala Thr Asn His Ala Ile Val Gln Thr Leu
    450                 455                 460 gtt cac ctt atg aac ccc gag tat gtc ccc aaa ccg tgc tgt gcg cca     1619
Val His Leu Met Asn Pro Glu Tyr Val Pro Lys Pro Cys Cys Ala Pro
465                 470                 475                 480 act aag cta aat gcc atc tcg gtt ctt tac ttt gat gac aac tcc aat     1667
Thr Lys Leu Asn Ala Ile Ser Val Leu Tyr Phe Asp Asp Asn Ser Asn
                485                 490                 495 gtc att ctg aaa aaa tac agg aat atg gtt gta aga gct tgt gga tgc     1715
Val Ile Leu Lys Lys Tyr Arg Asn Met Val Val Arg Ala Cys Gly Cys
            500                 505                 510 cac taa ctcgaaacca gatgctgggg acacacattc tgccttggat cctagatta       1771
His catctgcctt aaaaaacac ggaagcacag ttggaggtgg gacgatgaga ctttgaaact     1831
atctcatgcc agtgccttat tacccaggaa gattttaaag gacctcatta ataatttgct   1891
```

-continued

```
cacttggtaa atgacgtgag tagttgttgg tctgtagcaa gctgagtttg gatgtctgta    1951
gcataaggtc tggtaactgc agaaacataa ccgtgaagct cttcctaccc tcctccccca    2011
aaaacccacc aaaattagtt ttagctgtag atcaagctat ttggggtgtt tgttagtaaa    2071
tagggaaaat aatctcaaag gagttaaatg tattcttggc taaaggatca gctggttcag    2131
tactgtctat caaaggtaga ttttacagag aacagaaatc ggggaagtgg ggggaacgcc    2191
tctgttcagt tcattcccag aagtccacag gacgcacagc ccaggccaca gccagggctc    2251
cacggggcgc ccttgtctca gtcattgctg ttgtatgttc gtgctggagt tttgttggtg    2311
tgaaaataca cttatttcag ccaaaacata ccatttctac acctcaatcc tccatttgct    2371
gtactctttg ctagtaccaa agtagactg attacactga ggtgaggcta caaggggtgt    2431
gtaaccgtgt aacacgtgaa ggcagtgctc acctcttctt taccagaacg gttctttgac    2491
cagcacatta acttctggac tgccggctct agtaccttt cagtaaagtg gttctctgcc    2551
tttttactat acagcatacc acgccacagg gttagaacca acgaagaaaa taaaatgagg    2611
gtgcccagct tataagaatg gtgttagggg gatgagcatg ctgtttatga acggaaatca    2671
tgatttccct gtagaaagtg aggctcagat taaattttag aatatttct aaatgtcttt    2731 ttcacaatca tgtgactggg aaggcaattt catactaaac tgattaaata atacatttat    2791
aatctacaac tgtttgcact tacagctttt tttgtaaata taaactataa tttattgtct    2851
attttatatc tgttttgctg tggcgttggg ggggggccg ggcttttggg gggggggtt     2911 tgtttggggg gtgtcgtggt gtgggcgggc gg                                 2943
```

<210> SEQ ID NO 6
<211> LENGTH: 513
<212> TYPE: PRT
<213> ORGANISM: Homo sapiens

<400> SEQUENCE: 6

```
Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Ala Gly Gly Gln Leu Leu Gly Asp Gly Gly
        35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Leu Pro Arg Gly Glu Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190
```

```
Gly Ser Gly Gly Ala Ser Pro Leu Thr Ser Ala Gln Asp Ser Ala Phe
            195                 200                 205
Leu Asn Asp Ala Asp Met Val Met Ser Phe Val Asn Leu Val Glu Tyr
        210                 215                 220
Asp Lys Glu Phe Ser Pro Arg Gln Arg His His Lys Glu Phe Lys Phe
225                 230                 235                 240
Asn Leu Ser Gln Ile Pro Glu Gly Glu Val Val Thr Ala Ala Glu Phe
                245                 250                 255
Arg Ile Tyr Lys Asp Cys Val Met Gly Ser Phe Lys Asn Gln Thr Phe
            260                 265                 270
Leu Ile Ser Ile Tyr Gln Val Leu Gln Glu His Gln His Arg Asp Ser
        275                 280                 285
Asp Leu Phe Leu Leu Asp Thr Arg Val Val Trp Ala Ser Glu Glu Gly
        290                 295                 300
Trp Leu Glu Phe Asp Ile Thr Ala Thr Ser Asn Leu Trp Val Val Thr
305                 310                 315                 320
Pro Gln His Asn Met Gly Leu Gln Leu Ser Val Val Thr Arg Asp Gly
                325                 330                 335
Val His Val His Pro Arg Ala Ala Gly Leu Val Gly Arg Asp Gly Pro
            340                 345                 350
Tyr Asp Lys Gln Pro Phe Met Val Ala Phe Phe Lys Val Ser Glu Val
        355                 360                 365
His Val Arg Thr Thr Arg Ser Ala Ser Ser Arg Arg Arg Gln Gln Ser
        370                 375                 380
Arg Asn Arg Ser Thr Gln Ser Gln Asp Val Ala Arg Val Ser Ser Ala
385                 390                 395                 400
Ser Asp Tyr Asn Ser Ser Glu Leu Lys Thr Ala Cys Arg Lys His Glu
                405                 410                 415
Leu Tyr Val Ser Phe Gln Asp Leu Gly Trp Gln Asp Trp Ile Ile Ala
            420                 425                 430
Pro Lys Gly Tyr Ala Ala Asn Tyr Cys Asp Gly Glu Cys Ser Phe Pro
        435                 440                 445
Leu Asn Ala His Met Asn Ala Thr Asn His Ala Ile Val Gln Thr Leu
        450                 455                 460
Val His Leu Met Asn Pro Glu Tyr Val Pro Lys Pro Cys Cys Ala Pro
465                 470                 475                 480
Thr Lys Leu Asn Ala Ile Ser Val Leu Tyr Phe Asp Asp Asn Ser Asn
                485                 490                 495
Val Ile Leu Lys Lys Tyr Arg Asn Met Val Val Arg Ala Cys Gly Cys
            500                 505                 510
His

<210> SEQ ID NO 7
<211> LENGTH: 1878
<212> TYPE: DNA
<213> ORGANISM: Homo sapiens
<220> FEATURE:
<221> NAME/KEY: CDS
<222> LOCATION: (123)..(1418)

<400> SEQUENCE: 7
gggcgcagcg gggcccgtct gcagcaagtg accgacggcc gggacggccg cctgccccct      60
ctgccacctg gggcggtgcg ggcccggagc ccggagcccg ggtagcgcgt agagccggcg     120 cg atg cac gtg cgc tca ctg cga gct gcg gcg ccg cac agc ttc gtg       167
   Met His Val Arg Ser Leu Arg Ala Ala Ala Pro His Ser Phe Val
   1               5                  10                  15
```

```
gcg ctc tgg gca ccc ctg ttc ctg ctg cgc tcc gcc ctg gcc gac ttc      215
Ala Leu Trp Ala Pro Leu Phe Leu Leu Arg Ser Ala Leu Ala Asp Phe
         20                  25                  30 agc ctg gac aac gag gtg cac tcg agc ttc atc cac cgg cgc ctc cgc      263
Ser Leu Asp Asn Glu Val His Ser Ser Phe Ile His Arg Arg Leu Arg
     35                  40                  45 agc cag gag cgg cgg gag atg cag cgc gag atc ctc tcc att ttg ggc      311
Ser Gln Glu Arg Arg Glu Met Gln Arg Glu Ile Leu Ser Ile Leu Gly
 50                  55                  60 ttg ccc cac cgc ccg cgc ccg cac ctc cag ggc aag cac aac tcg gca      359
Leu Pro His Arg Pro Arg Pro His Leu Gln Gly Lys His Asn Ser Ala
             65                  70                  75 ccc atg ttc atg ctg gac ctg tac aac gcc atg gcg gtg gag gag ggc      407
Pro Met Phe Met Leu Asp Leu Tyr Asn Ala Met Ala Val Glu Glu Gly
 80                  85                  90                  95 ggc ggg ccc ggc ggc cag ggc ttc tcc tac ccc tac aag gcc gtc ttc      455
Gly Gly Pro Gly Gly Gln Gly Phe Ser Tyr Pro Tyr Lys Ala Val Phe
                 100                 105                 110 agt acc cag ggc ccc cct ctg gcc agc ctg caa gat agc cat ttc ctc      503
Ser Thr Gln Gly Pro Pro Leu Ala Ser Leu Gln Asp Ser His Phe Leu
             115                 120                 125 acc gac gcc gac atg gtc atg agc ttc gtc aac ctc gtg gaa cat gac      551
Thr Asp Ala Asp Met Val Met Ser Phe Val Asn Leu Val Glu His Asp
         130                 135                 140 aag gaa ttc ttc cac cca cgc tac cac cat cga gag ttc cgg ttt gat      599
Lys Glu Phe Phe His Pro Arg Tyr His His Arg Glu Phe Arg Phe Asp
 145                 150                 155 ctt tcc aag atc cca gaa ggg gaa gct gtc acg gca gcc gaa ttc cgg      647
Leu Ser Lys Ile Pro Glu Gly Glu Ala Val Thr Ala Ala Glu Phe Arg
160                 165                 170                 175 atc tac aag gac tac atc cgg gaa cgc ttc gac aat gag acg ttc cgg      695
Ile Tyr Lys Asp Tyr Ile Arg Glu Arg Phe Asp Asn Glu Thr Phe Arg
                 180                 185                 190 atc agc gtt tat cag gtg ctc cag gag cac ttg ggc agg gaa tcg gat      743
Ile Ser Val Tyr Gln Val Leu Gln Glu His Leu Gly Arg Glu Ser Asp
             195                 200                 205 ctc ttc ctg ctc gac agc cgt acc ctc tgg gcc tcg gag gag ggc tgg      791
Leu Phe Leu Leu Asp Ser Arg Thr Leu Trp Ala Ser Glu Glu Gly Trp
         210                 215                 220 ctg gtg ttt gac atc aca gcc acc agc aac cac tgg gtg gtc aat ccg      839
Leu Val Phe Asp Ile Thr Ala Thr Ser Asn His Trp Val Val Asn Pro
 225                 230                 235 cgg cac aac ctg ggc ctg cag ctc tcg gtg gag acg ctg gat ggg cag      887
Arg His Asn Leu Gly Leu Gln Leu Ser Val Glu Thr Leu Asp Gly Gln
240                 245                 250                 255 agc atc aac ccc aag ttg gcg ggc ctg att ggg cgg cac ggg ccc cag      935
Ser Ile Asn Pro Lys Leu Ala Gly Leu Ile Gly Arg His Gly Pro Gln
                 260                 265                 270 aac aag cag ccc ttc atg gtg gct ttc ttc aag gcc acg gag gtc cac      983
Asn Lys Gln Pro Phe Met Val Ala Phe Phe Lys Ala Thr Glu Val His
             275                 280                 285 ttc cgc agc atc cgg tcc acg ggg agc aaa cag cgc agc cag aac cgc     1031
Phe Arg Ser Ile Arg Ser Thr Gly Ser Lys Gln Arg Ser Gln Asn Arg
         290                 295                 300 tcc aag acg ccc aag aac cag gaa gcc ctg cgg atg gcc aac gtg gca     1079
Ser Lys Thr Pro Lys Asn Gln Glu Ala Leu Arg Met Ala Asn Val Ala
 305                 310                 315 gag aac agc agc agc gac cag agg cag gcc tgt aag aag cac gag ctg     1127
Glu Asn Ser Ser Ser Asp Gln Arg Gln Ala Cys Lys Lys His Glu Leu
320                 325                 330                 335
```

```
tat gtc agc ttc cga gac ctg ggc tgg cag gac tgg atc atc gcg cct    1175
Tyr Val Ser Phe Arg Asp Leu Gly Trp Gln Asp Trp Ile Ile Ala Pro
            340                 345                 350 gaa ggc tac gcc gcc tac tac tgt gag ggg gag tgt gcc ttc cct ctg    1223
Glu Gly Tyr Ala Ala Tyr Tyr Cys Glu Gly Glu Cys Ala Phe Pro Leu
            355                 360                 365 aac tcc tac atg aac gcc acc aac cac gcc atc gtg cag acg ctg gtc    1271
Asn Ser Tyr Met Asn Ala Thr Asn His Ala Ile Val Gln Thr Leu Val
            370                 375                 380 cac ttc atc aac ccg gaa acg gtg ccc aag ccc tgc tgt gcg ccc acg    1319
His Phe Ile Asn Pro Glu Thr Val Pro Lys Pro Cys Cys Ala Pro Thr
385                 390                 395 cag ctc aat gcc atc tcc gtc ctc tac ttc gat gac agc tcc aac gtc    1367
Gln Leu Asn Ala Ile Ser Val Leu Tyr Phe Asp Asp Ser Ser Asn Val
400                 405                 410                 415 atc ctg aag aaa tac aga aac atg gtg gtc cgg gcc tgt ggc tgc cac    1415
Ile Leu Lys Lys Tyr Arg Asn Met Val Val Arg Ala Cys Gly Cys His
                420                 425                 430 tag ctcctccgag aattcagacc ctttggggcc aagttttct ggatcctcca           1468 ttgctcgcct tggccaggaa ccagcagacc aactgccttt tgtgagacct tcccctccct   1528
atccccaact ttaaaggtgt gagagtatta ggaaacatga gcagcatatg cttttgatc    1588 agttttcag tggcagcatc caatgaacaa gatcctacaa gctgtgcagg caaaacctag    1648
caggaaaaaa aaacaacgca taaagaaaaa tggccgggcc aggtcattgg ctgggaagtc   1708
tcagccatgc acggactcgt ttccagaggt aattatgagc gcctaccagc caggccaccc   1768
agccgtggga ggaaggggc gtggcaaggg gtgggcacat tggtgtctgt gcgaaaggaa   1828
aattgacccg gaagttcctg taataaatgt cacaataaaa cgaatgaatg              1878
```

<210> SEQ ID NO 8
<211> LENGTH: 431
<212> TYPE: PRT
<213> ORGANISM: Homo sapiens

<400> SEQUENCE: 8

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
```

-continued

```
                        165                     170                     175
Tyr Lys Asp Tyr Ile Arg Glu Arg Phe Asp Asn Glu Thr Phe Arg Ile
            180                     185                     190

Ser Val Tyr Gln Val Leu Gln Glu His Leu Gly Arg Glu Ser Asp Leu
            195                     200                     205

Phe Leu Leu Asp Ser Arg Thr Leu Trp Ala Ser Glu Glu Gly Trp Leu
            210                     215                     220

Val Phe Asp Ile Thr Ala Thr Ser Asn His Trp Val Val Asn Pro Arg
225                     230                     235                     240

His Asn Leu Gly Leu Gln Leu Ser Val Glu Thr Leu Asp Gly Gln Ser
                    245                     250                     255

Ile Asn Pro Lys Leu Ala Gly Leu Ile Gly Arg His Gly Pro Gln Asn
                    260                     265                     270

Lys Gln Pro Phe Met Val Ala Phe Phe Lys Ala Thr Glu Val His Phe
                275                     280                     285

Arg Ser Ile Arg Ser Thr Gly Ser Lys Gln Arg Ser Gln Asn Arg Ser
            290                     295                     300

Lys Thr Pro Lys Asn Gln Glu Ala Leu Arg Met Ala Asn Val Ala Glu
305                     310                     315                     320

Asn Ser Ser Ser Asp Gln Arg Gln Ala Cys Lys Lys His Glu Leu Tyr
                    325                     330                     335

Val Ser Phe Arg Asp Leu Gly Trp Gln Asp Trp Ile Ile Ala Pro Glu
                340                     345                     350

Gly Tyr Ala Ala Tyr Tyr Cys Glu Gly Glu Cys Ala Phe Pro Leu Asn
            355                     360                     365

Ser Tyr Met Asn Ala Thr Asn His Ala Ile Val Gln Thr Leu Val His
        370                     375                     380

Phe Ile Asn Pro Glu Thr Val Pro Lys Pro Cys Cys Ala Pro Thr Gln
385                     390                     395                     400

Leu Asn Ala Ile Ser Val Leu Tyr Phe Asp Asp Ser Ser Asn Val Ile
                    405                     410                     415

Leu Lys Lys Tyr Arg Asn Met Val Val Arg Ala Cys Gly Cys His
                420                     425                     430
```